United States Patent

Thomson

Patent Number: 5,817,896
Date of Patent: Oct. 6, 1998

[54] CATALYTIC METHOD OF REPLACING HALOGEN IN HALOCARBONS

[75] Inventor: James Thomson, Dundee, Scotland

[73] Assignee: The University Court of The University of Dundee, Dundee, United Kingdom

[21] Appl. No.: 815,313

[22] Filed: Mar. 11, 1997

Related U.S. Application Data

[63] Continuation of Ser. No. 507,488, filed as PCT/GB94/00477 Mar. 11, 1994, published as WO94/22792 Oct. 13, 1994, abandoned.

[30] Foreign Application Priority Data

Mar. 26, 1993 [GB] United Kingdom .................. 9306334
Mar. 11, 1994 [GB] United Kingdom .................. 9404802

[51] Int. Cl.$^6$ ................................................ C07C 19/08
[52] U.S. Cl. ........................... 570/176; 502/329; 502/332; 502/333; 502/334; 502/344; 502/348; 502/355
[58] Field of Search ............................... 570/176; 502/329, 502/332, 333, 334, 344, 348, 355

[56] References Cited

U.S. PATENT DOCUMENTS 5,208,397  5/1993  Manogue et al. ..................... 570/176

FOREIGN PATENT DOCUMENTS

| | | |
|---|---|---|
| 0 241 760 | 10/1987 | European Pat. Off. . |
| 0 347 830 | 12/1989 | European Pat. Off. . |
| 0 459 463 | 12/1991 | European Pat. Off. . |
| 0 471 320 | 2/1992 | European Pat. Off. . |
| 0 508 660 | 10/1992 | European Pat. Off. . |
| 508660 | 10/1992 | European Pat. Off. . |
| 0 587 896 | 3/1994 | European Pat. Off. . |
| 0 594 858 | 5/1994 | European Pat. Off. . |
| 0 594 896 | 5/1994 | European Pat. Off. . |
| 1 172 349 | 7/1989 | Japan . |
| 1 573 832 | 8/1980 | United Kingdom . |
| 2 052 294 | 1/1981 | United Kingdom . |
| WO 89/00886 | 2/1989 | WIPO . |
| WO 92/18447 | 10/1992 | WIPO . |
| WO 93/09080 | 5/1993 | WIPO . |

*Primary Examiner*—C. Warren Ivy
*Assistant Examiner*—Lyman H. Smith
*Attorney, Agent, or Firm*—Ratner & Prestia

[57] ABSTRACT

As replacements for chlorofluorcarbons, hydro(chloro) fluorocarbons are synthesized by hydrogenating chlorofluorocarbons over a Pd/ZnO/γ—Al$_2$O3 catalyst. The ZnO is partially reduced before use and assists the Pd to function catalytically for days instead of hours despite the evolution of halogen.

20 Claims, No Drawings

CATALYTIC METHOD OF REPLACING HALOGEN IN HALOCARBONS

This application is a continuation of application Ser. No. 08/507,488 filed Feb. 29, 1996 now abandoned.

This application is a 35 U.S.C. 371 National Stage filing of PCT/GB94/00477 published as WO94/22792 on Oct. 13,1994.

This invention relates to a catalytic method of replacing halogen in halo-substituted hydrocarbons by hydrogen, and especially when only a selected member of the halogen family is replaced. Thus the method may be especially useful in the hydrogenation of halocarbons for example chlorofluorocarbons (CFCs), and hydrohalocarbons for example hydrochlorofluorocarbons (HCFCs), especially where the chlorine is preferentially or selectively replaced by hydrogen.

Chlorofluorocarbons (CFCs) have been widely used for their excellence as aerosol propellants, refrigerants, cleaning solvents and foam blowing agents. However, it is now appreciated that CFCs have a harmful effect on the stratospheric ozone layer, with one CFC molecule being able to decompose up to $10^5$ ozone molecules, thus severely damaging the protection which the ozone layer affords the earth's surface against UV radiation. Therefore it has been internationally agreed to cease CFC production by 1996, except as chemical precursors. As a result it has become important to provide compounds which have similar technical properties to those of CFCs but which are environmentally acceptable.

For some 40% of the former demand for CFCs, the only alternatives which are practical with current technology are HCFCs and hydrofluorocarbons (HFCs), and these can best be synthesised by replacing chlorine in CFCs by hydrogen. Catalysts that have been proposed for this process include palladium chloride supported on activated carbon (JP 01,319,442 25 Dec. 1989) or a 5% loading of palladium on activated carbon (UK Patent 1578933) or palladium supported on aluminium fluoride (European Patent Application 328127) or palladium supported on alumina (German Offen. 3917575). A problem with these catalytic systems is that the conversion yield of CFCs to ISFCs is very low, typically around 5% and deactivate after a relatively short time, such as 2 hours. These palladium systems are also used to produce HFCs by removing chlorine from the alternative feedstock of chlorofluorohydrocarbons (e.g. HCFC-124, $CHFClCF_3$).

According to the present invention, there is provided a method of replacing halogen in halo-substituted hydrocarbon by hydrogen, comprising exposing the halo-substituted hydrocarbon to a catalyst in the presence of a source of hydrogen, the catalyst comprising a catalytic metal, characterised in that the catalyst also comprises a material which either has a greater affinity for halogen than has the catalytic metal, or stabilises the zero oxidation state of the catalytic metal, or both, so as to resist adsorption of halogen on the catalytic metal surface. Preferably the catalytic metal is palladium, platinum, rhodium, ruthenium, silver, gold or gallium, especially palladium and/or platinum. Preferably the said material contains metal different from the catalytic metal, such as zinc, aluminium, silver, platinum, nickel, gold or gallium, and it may further contain combined oxygen, thus comprising or derived from an oxide, nitrate or organometallic compound such as a salt, e.g. carboxylate e.g. acetate, an especially effective combination being palladium and zinc (preferably as a zinc-oxgyen compound). Preferably the molar ratio of catalyst metal to material is from 1:10 to 1:1, such as from 1:5 to 1:2. The catalyst may be supported on an inert carrier such as alumina, preferably having a surface area of at least 50 $m^2/g$. The method is preferably performed at a temperature of from 280 to 450° C., such as from 350to 4350° C., especially 400–425° C. At low temperatures, halo-substituted hydrocarbons tend to remain unreacted, while at excessive temperatures, they can react with the catalyst support.

Reactions especially amenable to the catalytic method set forth above are those wherein the halosubstituted carbon is a hydrochlorofluorocarbon or a chlorofluorocarbon, especially wherein chlorine rather than fluorine is replaced by hydrogen, and, if suitably carried out, the main product of the method according to the invention can indeed be a fluorocarbon or a hydrofluorocarbon, i.e. all the chlorine has been replaced by hydrogen. Most suitably, the hydrocarbon is aliphatic, e.g. an alkane, e.g. methane or ethane, and thus a typical method according to the invention would be to convert $CCl_2F$—$CClF_2$ to $CH_3$—$CF_3$ (an isomerisation does appear to occur).

The invention also extends to the catalyst as set forth above.

By providing the said material in the catalyst, the surface of the catalytic metal has low affinity for halogen freed from the halocarbon during hydrogenation. An important factor in the low yields obtained with previously proposed catalysts is that the active sites on the palladium surface become occupied by halogen or hydrogen halide, with consequent lessening of the catalytic effect of the palladium; the active sites are shielded from the reactants in the hydrogenation. With the catalyst of the present invention. the halogen or hydrogen halide released in the hydrogenation is attracted preferentially to the said material instead of to the catalytic metal, so the active sites on the latter remain available to the reactants for a longer time.

The components of the catalyst may be in the form of an alloy or close admixture, but other types of combination may also prove useful.

The invention will now be described by way of illustration in the following Examples.

EXAMPLE 1

The catalyst of this embodiment of the invention was prepared as follows: 1g of Degussa 'C' γ—alumina support (to give high surface area) was impregnated with 5 wt% of palladium nitrate (50 mg) and a two-fold stoichiometric amount of zinc using zinc oxide (70 mg). The resultant cake was broken up and loaded into a Pyrex reactor tube where it was calcined at 503K for 6 hours followed by reduction or partial reduction at 503K for 18 hours with a 9:1 mixture of dinitrogen and dihydrogen flowing at 100 ml $min^{-1}$. After this reduction, which is believed to give rise to a zinc oxide which is rich in elemental zinc especially at the surface, the reactor temperature was increased to 773K for 4 hours prior to cooling to room temperature.

1,1,2-Trichlorotrifluoroethane (CFC-113) was passed over the resulting amount of catalyst at 513K with a mass flow of 96 microlitres $min^{-1}$ together with a stoichiometric excess of dihydrogen, and the reactor eluant was analysed by online gas chromatographic facilities. The analysis showed the presence of 1,1,2-trifluoroethane and 1-chloro-1,2,2-trifluoroethane. The conversion from the CFC-113 was greater than 60%, and the catalyst performed at this rate of conversion over a period of 48 hours and beyond without any substantial loss of activity.

Hydrogen chloride released in the hydrogenation of the CFC-113 is adsorbed on the zinc of the catalyst to form zinc chloride, in preference to adsorption on the palladium. The high yield is obtained by virtue of the palladium remaining free of this contaminant and continuing to provide active sites for the reactants. The zinc chloride can subsequently be reduced to reconstitute the zinc metal in the catalyst.

Examples 2–7

In all these Examples (except 6, which is a comparative example where no palladium was used), the catalyst was Pd/ZnO/γ—Al$_2$O$_3$ (or Pd/Zn acetate/γ—Al$_2$O$_3$).

Palladium nitrate hydrate was used as the precursor for the catalysts. The catalyst support was gamma alumina having a surface area of 110 m$^2$/g. Zinc oxide or zinc acetate dihydrate was added to improve catalyst performance.

The amount of palladium nitrate hydrate shown in the Table together with 1 gram of gamma alumina and the appropriate zinc compound were weighed into an evaporating dish and dissolved in 10 ml of deionised distilled water. The solution was then dried on a heating mantel. The resulting cake was ground with an agate pestle and mortar prior to calcination.

TABLE

| EXAMPLE | MOLE RATIO | γ-Al$_2$O$_3$ (grams) | Pd(NO$_3$)$_2$xH$_2$O (grams) | ZnO/Zn(ac)$_2$(H$_2$O)$_2$ (grams) |
|---|---|---|---|---|
| 2 | Pd:ZnO = 1:2 | 1.000 | 0.108 | 0.076 |
| 3 | Pd:ZnO = 1:1 | 1.000 | 0.108 | 0.038 |
| 4 | Pd:ZnO = 2:1 | 1.000 | 0.108 | 0.019 |
| 5 | Pd:ZnO = 1:4 | 1.000 | 0.108 | 0.152 |
| 6 | No Pd | 1.000 | — | 0.076 |
| 7 | Zn(ac)$_2$ used | 1.000 | 0.108 | 0.205 |

1 gram of the impregnated catalyst was placed in a reaction tube and was first calcined at 4500° C. for 6 hours, under 10% hydrogen in oxygen-free nitrogen, flowing at a rate of 30 ml/min. The calcination was followed by treatment for 16 hours at 2300° C. under 10% hydrogen in oxgyen-free nitrogen, flowing at a rate of 30 ml/min, then recalcination at 450° C. for 6 hours under 10% hydrogen in oxygen-free nitrogen, flowing at a rate of 30 ml/min. Finally the catalyst was held under 10% hydrogen in oxygen-free nitrogen at 2300° C. This treatment reduced or partially the zinc compound.

Oxygen-free nitrogen was set at a rate of 13.5 ml/min flowing through a reservoir containing the CFC 113 feed (CCl$_2$F—CClF$_2$). This have a trichlorotrifluoroethane flow rate of 43 μl/min. Hydrogen flow through the bed was set at 1.5 ml/min.

The reactor pressure was maintained at 900 torr. Runs were performed with the catalyst bed at various temperatures from 70to 450° C. The performance of each catalyst is shown in the following tables:

EXAMPLE 2

| TEMPERATURE °C. | CONVERSION of feedstock CFC 113 (CCl$_2$FCClF$_2$) | Of the reacted products, percentage which was: | | |
|---|---|---|---|---|
| | | HFC 143a CF$_3$CH$_3$ | HCFC 133a CF$_3$—CH$_2$Cl | OTHERS |
| 70 | 0.00 | — | — | — |
| 115 | 0.00 | — | — | — |
| 152 | 0.49 | 100.00 | — | — |
| 168 | 0.54 | 100.00 | — | — |
| 196 | 1.70 | 100.00 | — | — |
| 200 | 3.88 | 100.00 | — | — |
| 230 | 4.62 | 100.00 | — | — |
| 250 | 4.63 | 100.00 | — | — |
| 275 | 5.62 | 99.32 | 0.68 | — |
| 300 | 9.18 | 88.55 | 11.45 | — |
| 316 | 8.22 | 85.89 | 14.03 | 0.09 |
| 360 | 10.69 | 69.12 | 16.90 | 13.98 |
| 375 | 18.52 | 43.95 | 44.04 | 12.01 |
| 400 | 66.14 | 29.38 | 64.26 | 6.35 |
| 450 | 95.30 | 22.92 | 70.91 | 6.17 |

EXAMPLE 3

| TEMPERATURE °C. | CONVERSION % | Of the reacted products, percentage which was: | | | |
|---|---|---|---|---|---|
| | | HFC 143a | HCFC 133a | HCFC 123a CHClF—CClF$_3$ | OTHERS |
| 280 | 15.99 | 38.82 | 59.76 | 1.42 | — |
| 330 | 12.91 | 15.34 | 82.53 | 2.13 | — |
| 370 | 19.06 | 8.95 | 83.16 | 5.26 | 2.63 |
| 385 | 20.58 | 30.23 | 59.17 | 5.42 | 5.17 |
| 390 | 42.90 | 64.45 | 22.07 | 7.38 | 6.10 |
| 400 | 49.60 | 67.72 | 14.40 | 10.15 | 7.73 |

EXAMPLE 4

| TEMPERATURE °C. | CONVERSION % | Of the reacted products, percentage which was: | | | |
|---|---|---|---|---|---|
| | | HFC 143a | HCFC 133a | HCFC 123a | OTHERS |
| 230 | 7.19 | 10.83 | 18.94 | 54.14 | 16.08 |
| 280 | 8.39 | 4.81 | 17.34 | 58.04 | 19.81 |
| 330 | 10.09 | 3.22 | 11.45 | 57.21 | 28.10 |
| 380 | 19.79 | 2.67 | 2.67 | 34.66 | 60.00 |

EXAMPLE 5

| TEMPERATURE °C. | CONVERSION % | Of the reacted products, percentage which was: | | |
|---|---|---|---|---|
| | | HFC 143a | HCFC 133a | HCFC 123a |
| 280 | 61.93 | 98.41 | — | 1.59 |
| 330 | 77.14 | 98.11 | 0.55 | 1.26 |
| 380 | 83.13 | 97.00 | 1.86 | 1.14 |
| 400 | 83.85 | 93.77 | 4.42 | 1.81 |
| 420 | 94.55 | 85.14 | 13.42 | 1.43 |
| 450 | 97.96 | 93.93 | 3.18 | 2.89 |

EXAMPLE 6 (comparative)

1 gram of the ZnO/γ—Aly$_2$O$_3$ catalyst, with no palladium, was calcined and reacted as described. The catalyst bed was maintained at temperatures between 230 and 4200° C. No hydrodechlorinated products were detected. A white powdery deposit was ob se rved on the reaction tube when working at catalyst bed temperatures in the region of 230–300° C. This was suspected to be a z inc h alide, possibly ZnCl$_2$ as its boiling point is in this region.

EXAMPLE 7

|  |  | Of the reacted products, percentage which was: | |
| --- | --- | --- | --- |
| TEMPERATURE °C. | CONVERSION % | HFC 143a | HCFC 133a |
| 230 | 95.27 | 58.82 | 41.18 |
| 280 | 96.92 | 73.56 | 26.44 |
| 380 | 97.83 | 77.77 | 22.23 |
| 400 | 94.21 | 84.21 | 15.79 |
| 420 | 91.83 | 91.48 | 8.52 |
| 450 | 88.28 | 92.19 | 7.81 |

1 gram of Pd/C catalyst (Aldrich 5% palladium on activated carbon) was calcined at 230° C. for 2 hours and reacted as described in UK Patent 1578933. Eluant samples were taken on a half hourly basis. Initially a conversion of 4–5% was obtained; however after just 2 hours the catalyst became deactivated and the reaction ceased.

The conversion efficiency of a catalyst acco rd ing to the present invention, on the other hand, showed a deactivation rate of 0.6% per hour and thus remained at at least half its original value for 20–25 hours, then falling more sharply to around 4% at 30 hours .

I claim:

1. A method of replacing halogen in halo-substituted hydrocarbon by hydrogen, comprising exposing the halo-substituted hydrocarbon to a catalyst in the presence of a source of hydrogen, the catalyst comprising palladium, rhodium, ruthenium, silver, gold or gallium, characterised in that the catalyst also comprises a material which either has a greater affinity for halogen than has the catalytic metal, or stabilises the zero oxidation state of the catalytic metal, or both, wherein the said material contains zinc, aluminium or, provided the catalyst does not comprise gallium, gallium.

2. A method according to claim 1, wherein the said material is present in elemental form alloyed or closely admixed with said catalytic metal, and/or contains combined oxygen.

3. A method according to claim 2, wherein said material comprises or is derived from an oxide or nitrate or organo-metallic compound.

4. A method according to claim 1, wherein the catalyst is supported on an inert carrier.

5. A method according to claim 4, wherein the inert carrier is a ceramic.

6. A method according to claim 5, wherein the ceramic is alumina.

7. A method according to claim 1, wherein the halosubstituted carbon is a hydrochlorofluorocarbon or a chlorofluorocarbon.

8. A method according to claim 7, wherein chlorine rather than fluorine is replaced by hydrogen.

9. A method according to claim 1, wherein the hydrocarbon is aliphatic.

10. A method according to claim 9, wherein the hydrocarbon is an alkane.

11. A method according to claim 1, wherein the molar ratio of catalyst metal to material is from 1:10 to 1:1.

12. A method according to claim 11, wherein the said ratio is 5 from 1:5 to 1:2.

13. A method according to claim 1, when performed at a temperature of from 280 to 4500° C.

14. A method according to claim 13, when performed at a temperature of from 350 to 435° C.

15. A catalyst comprising a catalytic metal being palladium, rhodium, ruthenium, silver, gold or gallium, and a material having a greater affinity for halogen than does the catalytic metal, wherein said material contains zinc, aluminum, or, subject to the catalytic metal not being gallium, gallium.

16. A catalyst according to claim 15, wherein the said material is present in elemental form alloyed or closely admixed with said catalytic metal, and/or contains combined oxygen.

17. A catalyst according to claim 16, wherein said material comprises or is derived from an oxide or nitrate or organometallic compound.

18. A catalyst according to claim 15, wherein the catalyst is supported on an inert carrier.

19. A catalyst according to claim 18, wherein the inert carrier is a ceramic.

20. A catalyst according to claim 19, wherein the ceramic is alumina.

* * * * *